United States Patent [19]

Swanson

[11] Patent Number: 5,372,944
[45] Date of Patent: Dec. 13, 1994

[54] METHOD FOR CONVERSION OF HALOGENATED HYDROCARBONS TO HALOHYDRINS

[75] Inventor: Paul E. Swanson, Midland, Mich.

[73] Assignee: The Dow Chemical Company, Midland, Mich.

[21] Appl. No.: 137,242

[22] Filed: Oct. 14, 1993

[51] Int. Cl.$^5$ .............. C12P 1/04; C12N 1/20; C12N 9/00
[52] U.S. Cl. .................. 435/252.1; 435/262; 435/822; 435/170
[58] Field of Search .............. 435/252.1, 262, 170, 435/822

[56] References Cited

U.S. PATENT DOCUMENTS 5,155,043  10/1992  Murakami et al. .................. 435/280

OTHER PUBLICATIONS

ATCC, "Catalogue of Bacteria & Bacteriophages", pp. 271–272, 18th Ed., 1992.

*Primary Examiner*—Herbert J. Lilling
*Attorney, Agent, or Firm*—Duane C. Ulmer; Ronald G. Brookens; James M. Pelton

[57] ABSTRACT

A process for converting halogenated aliphatic hydrocarbons to halohydrins using a microorganism selected from Rhodococcus species ATCC 55388 and mutants thereof are described.

4 Claims, No Drawings

METHOD FOR CONVERSION OF HALOGENATED HYDROCARBONS TO HALOHYDRINS

FIELD OF THE INVENTION

The present invention relates to conversion of halogenated hydrocarbons to halohydrins using microorganisms.

BACKGROUND OF THE INVENTION

A large amount of short-chain halogenated aliphatic hydrocarbons are produced for use as organic solvents, degreasing agents, pesticides, intermediates for the synthesis of various other organic compounds and as ingredients in the manufacture of plastics. The extensive use of these halogenated compounds in industrial processes creates a substantial problem in the disposal of the waste material.

Halogenated aliphatic hydrocarbons as a byproduct in a chemical process can be burned to produce heat, thus, yielding some recovery from a waste product. When the halogenated aliphatic hydrocarbon is released into the environment, removal from the environment occurs by microbial biodegradation. Biodegradation of halogenated aliphatic hydrocarbons results in the formation of carbon dioxide, water and hydrochloric acid when the halogen is a chloride.

The biodegradation of halogenated aliphatic hydrocarbons to carbon dioxide, water and hydrochloric acid by select microorganisms is disclosed in U.S. Pat. Nos. 4,853,334 and 4,877,736. A process for the decomposition of chlorinated aliphatic hydrocarbons, without specifying the microorganism involved is described in U.S. Pat. No. 4,749,491. In addition, the aerobic metabolism of trichloroethylene by Acinetobacter sp. has been reported by Nelson et al., *Appl. Environ. Microbiol.* 52:383–384 (1986). An overview of the degradation of halogenated aliphatic compounds in the environment is given in Vogel et al., *Environ. Sci. Technol.*, 21: 722–736 (1987).

Rather than burn the halogenated aliphatic hydrocarbons or depend on the biodegradation of the compound in nature, it would be advantageous to have a process whereby the halogenated aliphatic hydrocarbons are converted to a valuable intermediate for use in production of other useful products, such as a chemical intermediate in preparation of polyethers to form polyurethanes or preparation of glycols and polyglycols to form lubricants, surfactants, emulsifiers, etc.

SUMMARY OF THE INVENTION

The present invention provides a biologically pure culture of a microorganism having the identifying characteristics of a representative strain of Rhodoccocus species ATCC 55388 and mutant thereof. The present invention also provides a process of converting chlorinated aliphatic hydrocarbons to halohydrins comprising contacting a microorganism representative of the strain Rhodoccocusspecies ATCC 55388 with a chlorinated aliphatic hydrocarbon in the presence of a medium which does not substantially inhibit the Rhodoccocus species.

In another embodiment, the present invention provides a process for producing halohydrins comprising contacting a cell-free extract from a microorganism having the identifying characteristics of a representative strain of Rhodoccocus species 55388 with a halogenated aliphatic hydrocarbon in the presence of a liquid medium.

DETAILED DESCRIPTION

The present invention relates to the isolation and use of a Rhodococcusspecies deposited as ATCC number 55388. The Rhodococcusspecies is able to convert halogenated aliphatic hydrocarbons to halohydrins without substantial degradation of the substrate to carbon dioxide and water. The conversion of halogenated aliphatic hydrocarbons to halohydrins when contacted with the Rhodococcus species occurs by an enzymatic hydrolytic dehalogenation. Since the conversion is enzymatic, the conversion can be performed in any suitable medium which does not substantially affect the enzymes of the Rhodococcusspecies responsible for the dehalogenation, in particular a haloalkane dehalogenase (E.C. 3.8.1). The production of halohydrins from halogenated aliphatic hydrocarbons can also be done utilizing a cell-free extract from Rhodococcus species. The conversion can therefore take place during growth of the Rhodococcus species under aerobic conditions in the presence of a nutrient medium. Conversion can also take place by contacting the halogenated aliphatic hydrocarbon with Rhodococcus species in a non-growth medium, such as a buffer system or by contacting a cell-free extract with the halogenated aliphatic hydrocarbon in a suitable medium, such as a buffer system. As used herein, a medium which does not substantially inhibit the Rhodococcus species therefore means a medium which does not substantially inhibit the enzymatic activity for conversion of the halogenated aliphatic hydrocarbons to halohydrins.

Halogenated aliphatic hydrocarbons subject to conversion include $C_2$–$C_{10}$ saturated aliphatic hydrocarbons which have two or more halogen groups attached, wherein at least two of the halogens are on adjacent carbon atoms. Such aliphatic hydrocarbons include volatile chlorinated aliphatic (VCA) hydrocarbons. VCA's include, for example, aliphatic hydrocarbons such as dichloroethane, 1,2-dichloro-propane, 1,2-dichlorobutane and 1,2,3-trichloropropane. The preferred substrates are 1,2-dichloropropane, 1,2-dichlorobutane and 1,2,3-trichloropropane. The term "halogenated hydrocarbon" as used herein means a halogenated aliphatic hydrocarbon.

As used herein the term "halogen" means chlorine, bromine and iodine. The preferred halogen is chlorine.

When it is desired to produce the halohydrin with an actively growing culture, any culture medium can be employed in which the genus Rhodococcus can usually grow. The culture medium generally contains assimilable sources of carbon, nitrogen, inorganic salts and vitamins. For example, sugars such as glucose, sucrose and maltose can be used as a carbon source, ammonium sulfate, ammonium phosphate, urea, yeast extract, meat extract or peptone can serve as a nitrogen source.

Microorganisms capable of converting target halogenated aliphatic hydrocarbons can be selected from mixed cultures by growing the culture in the presence of an inducer capable of stimulating biodegradation, under conditions such that the culture is enriched for microorganisms capable of converting the target hydrocarbon. Pure cultures of such microorganisms can then be isolated by subculturing the enriched population using techniques well known to one skilled in the art.

The microorganism of the present invention is cultured in the conventional manner. For example, the microorganism is preferably cultured in the culture medium of pH ranging from about 4.0 to 9.5 at a temperature of from 20°–45° C. for 10–96 hours under aerobic conditions. Most preferably the microorganism is cultured at a pH of 7.0 and a temperature of 28° C. for about 24 hours.

The halogenated hydrocarbon substrate concentration is generally added to a medium at the level of solubility of the halogenated hydrocarbon. The concentration of the halogenated hydrocarbon is thus generally from about 0.005 percent to about 0.25 percent (w/v). Preferably, the concentration of the halogenated hydrocarbon is from about 0.005 percent to about 0.10 percent. More preferred is a concentration of halogenated hydrocarbon from about 0.005 percent to about 0.05 percent in the medium. The substrate may be added to the reaction solution initially, or be added based upon a batch-type process or continuous feed. The reaction is usually carried out with shaking or stirring. Although the reaction time may vary depending on the reaction condition such as the substrate concentration or the amount of the enzyme, the reaction condition is preferably selected so that the reaction is completed within 120 hours.

PREFERRED EMBODIMENT

Microorganisms

A variety of soil and water samples were obtained from various sites in Midland County, Mich., including fresh sludge from two waste treatment aeration ponds at The Dow Chemical Company and estuarine mud from the Tittabawassee and Chippewa rivers.

Enrichment procedures to obtain microorganisms capable of growth on halocarbon substrates were done using minimal medium #1 (MM1) or minimal medium #1 X4P (MM1X4P). MM1 contains per liter: Potassium phosphate, dibasic, 1.55 g; sodium phosphate, monobasic monohydrate, 0.85 g; ammonium sulfate, 2.0 g; sodium nitrate, 2.0 g; and magnesium chloride hexahydrate, 0.1 g. To each liter of the above solution, 1 mL of a trace metals solution containing per liter; disodium ethylenediaminetetraacetic acid (EDTA), 500 mg; ferrous sulfate heptahydrate, 200 mg; zinc sulfate heptahydrate, 10 mg; manganese chloride tetrahydrate, 3.0 mg; boric acid, 30 mg; cobalt chloride hexahydrate, 20 mg; calcium chloride dihydrate, 1.0 mg; nickel chloride hexahydrate, 2.0 mg; and sodium molybdate dihydrate, 3.0 mg was added. Also to each liter, 10 mL of a vitamin mixture containing per liter: biotin, 20 mg; folic acid, 20 mg; pyridoxine, 100 mg; thiamine hydrochloride, 50 mg; riboflavin, 50 mg; nicotinic acid, 50 mg; D,L-calcium pantothenate, 50 mg; cyanocobalamin (B12), 1 mg; para-amino hydroxybenzoic acid, 50 mg; and lipoic acid, 50 mg was added. The pH of the media was adjusted to 7.0 prior to sterilization.

MM1X4P was identical to MM1 except that levels of the two phosphate salts were quadrupled to improve buffering.

Three separate enrichment regimens were utilized for obtaining microorganisms capable of growing on halocarbon substrates:

(1) Continuous dilution with a small fermenter;
(2) Solid minimal media plates inside desiccator jar with halocarbon vapor; and
(3) Shake flasks with liquid minimal media/sequential dilution.

(1) Continuous dilution with a small fermenter: A 500 mL Bio-Stir jar equipped for continuous operation was sterilized with 500 mL MM1. With stirring and aeration with sterile air, a mixture of carbon sources; glucose, sodium acetate, sodium succinate, glycerol, glycine, and arginine were each added at a concentration of about 0.1 g/L followed by addition of 5–10 mLs of a microbial inoculum. Dilution was then initiated at 0.02 $hr^{-1}$ [1] using MM1 containing from 100 to 200 ppm of either 1,2-dichloropropane or a mixture of 1-chlorobutane, 2-chlorobutane, and 1-chloro-2-methylpropane as the sole carbon sources(s). Viable organisms were monitored periodically by dilution and plating on nutrient media. When steady state was evident, the dilution rate was increased incrementally to establish new steady states. When the dilution rate had exceeded the growth rate (washout), microorganisms were rescued on nutrient media for isolation and further screening. This enrichment method required from 10 days to 4 weeks.

(2) Solid minimal media plates inside desiccator jar with halocarbon vapor: Appropriate dilutions of various inoculum were prepared in sterile saline and 0.1 mL aliquots spread plated onto MM1 plates with no carbon source. Plates were placed into a glass desiccator containing several drops of a halocarbon in a small beaker. The desiccators were closed and growth monitored after 7–10 days. Visible colonies were transferred to nutrient media using sterile toothpicks.

(3) Shake flasks with liquid minimal media/sequential dilution: One liter (1000 mL) shake flasks containing 200 mL of sterile MM1X4P were inoculated with inoculum from the various soil and water sources. The halocarbon substrate was provided as a vapor using the method described by Gibson, et al., *Biochem.*, 9:3795–3802 (1968) and was added every 3–4 days. Beginning on a weekly basis, cultures were diluted 1 to 10 into fresh media. Over a period of weeks, growth was monitored visually and dilution frequency increased as growth became evident. Dominant organisms were rescued by plating onto solid nutrient media.

A combination of methods 2 & 3 was also utilized. Method 3 was used initially to dilute out non-halocarbon utilizers prior to plating on minimal media for isolation using Method 2.

All microorganisms obtained from halocarbon enrichments were streaked for isolation on nutrient agar. Pure cultures were characterized by gram staining and evaluated microscopically for general morphology. Further identification as to genus and species was performed by Five Star Laboratories, Branford, Conn. using fatty acid profile data bases. Organisms were routinely maintained and transferred on nutrient agar slants stored at 4° C.

To evaluate candidate organisms for cell free hydrolytic dehalogenase activity, cultures were inoculated from slants into 25 mL nutrient media in a 125 mL shake flask. Following overnight growth, 5 mLs was inoculated into 25 mL enriched media in a 1.0 liter flask. The composition of enriched media per liter is as follows:

potassium phosphate, dibasic, 1.5 g;
sodium phosphate, monobasic dodecahydrate, 1.5 g;
ammonium nitrate, 4.0 g;
magnesium sulfate heptahydrate, 0.2 g;
yeast extract, 50 g;
disodium succinate, 10 g;

YM broth, 22 g. pH adjusted to 7.2 prior to sterilization.

Following overnight growth, 50 µl of 1-chlorobutane was added to induce the dehalogenase. After 24 hours induction, cells were harvested by centrifugation, resuspended in cold 10mM Tris sulfate/1 mM disodium EDTA, pH=7.5, and disrupted by sonication. Cell debris was removed by centrifugation at 10,000 rpm for 30 minutes, cell free extracts dialyzed overnight against the same buffer, and assayed without dilution for dehalogenase activity.

To evaluate kinetics and selectivity of various mutants with respect to conversion of the target halocarbons, 1,2-dichloropropane (DCP), 1,2-dichloro-butane (DCB) and 1,2,3-trichloropropane (TCP) cultures were first inoculated from slants into 25 mL nutrient media in a 125 mL flask and grown overnight. Five mL were inoculated into 50 mL of MM1X4P containing 5 g/L disodium succinate in a 250 mL flask. Following 4 hours of growth and again at 8 hours, 10 µl of 1-chlorobutane was added for induction of the dehalogenase. Following 24 hours growth, cells were harvested by centrifugation and resuspended into 50 mL of fresh sterile MM1X4P and transferred to a sterile 250 mL shake flask equipped with a bulb feeder as described by Gibson, et al., supra. DCP, DCB, and TCP were added to bulb feeders and reaction progress monitored by gas chromatography (GC). Throughout the protocol, volumes were modified as needed to provide higher concentrations of cells and/or to provide identical batches of induced cells for comparative studies.

All liquid culturing was performed at 28° C. at 150 rpm shaking in a New Brunswick G-26 Psycrotherm or G-25 floor model incubator.

Analytical Methods

For gas chromatography (GC) analysis of halogenated metabolites, cultures were centrifuged briefly to remove cells, saturated with sodium sulfate, and an equivalent volume of methylene chloride added. The suspension was vortexed vigorously, centrifuged to break the emulsion and the methylene chloride phase removed.

Analysis of all halocarbon substrates and products from culture broths was done by GC using a Hewlett Packard 5710 equipped with a 7671A Autoinjector with the following protocol:

Column: DB-624, 30 meter. 0.53 mm Megabore, J&W Scientific
Injection: Splitless; 2 µL
Detection: FID
Program: 2 minutes at 60° C. then to 150° C. at a gradient of 8° C./min, held at 150° C. for 2 minutes.
Injector: 150° C.
Detector: 250° C.

All halocarbon, halohydrin, or epoxide standards were prepared individually (w/v) in methylene chloride as 1,000 ppm stock solutions and stored at 4° C. These were diluted to 25 ppm mixed standards in methylene chloride for frequent GC standardization by the external standard method. For propylene halohydrin, available as a technical mixture of 1-chloro-2-propanol and 2-chloro-1-propanol, the FID response factor was assumed to be equivalent for the two isomers, and was standardized accordingly.

Free chloride or bromide was assayed qualitatively using a chloride electrode (Orion), or quantitatively using the colorimetric method (430 nm) described by J. G. Bergmann, et al., Anal. Chem., 29:241–243 (1957).

Hydrolytic dehalogenase enzyme activity was evaluated by adding an appropriate amount of cell free extract or enzyme preparation to 5.0 mL of 100 mM glycine buffer, pH=9.0 in a 7 mL glass vial. The halogenated substrate (5.0 µl) and a small stir bar were added, and the vial capped. Reaction was initiated by transfer to a 30° C. water bath equipped with a magnetic stirrer. Periodically 1.0 mL samples were removed and assayed for free halide. Rates were determined after correcting for non-enzymatic hydrolysis with an appropriate blank. A standard curve was prepared using sodium chloride.

Analysis for optical activity of microbially produced 2,3-dichloro-1-propanol was determined independently using two methods. Polarimetry was performed using a Horiba SEPA 200 polarimeter, and optical rotations were compared to a standard curve to provide an estimate of enantiomeric excess. Gas chromatographic separation of 2,3-dichloro-1-propanol enantiomers was done using a 5 percent phenyl silicone/95 percent methyl silicone column (DB-5 column, J&J scientific) following formation of diesteromeric monoesters with S(+)-2-phenyl butyric acid. Enantiomeric composition of DCP, DCB, and respective halohydrins can also be monitored using a derivatized cyclodexdrin gas chromatography column (CHIRALDEX ™ type B-TA Column, Advanced Separation Technologies, Inc.). Enantiomeric excess was determined by a comparison of peak areas.

Protein was determined by the method of Lowry, J. Biol. Chem., 193:265–275 (1951) and sodium dodecyl sulfate polyacrylamide gel electrophoresis (SDS PAGE electrophoresis) was performed according to the method of Laemmli, Nature, 277:680–685 (1970) using precast 4 to 20 percent Acrylamide Bio-Rad Mini-Protean II Gels.

Mutagenesis Techniques

Nitrous acid was used throughout as a mutagen using the protocol described initially by D. O. Schwartz et al., Genetics, 61:371 (1969). Kill curves were initially established with the wild type microorganism and exposure times giving approximately 0.1 percent survival were used throughout.

Isolation of alcohol dehydrogenase negative mutants using a post mutagenic treatment with bromoethanol was modified from the technique described in D. B. Janssen et al., J. Bacteriol., 171:6791–6799 (1989). A 4 hour-outgrowth at 30° C. in the presence of 5 mM ethanol and 5 mM sodium citrate was performed following quenching of the mutagen and resuspension of cells in fresh MM1. Cells were centrifuged and the pellet resuspended in MM1 and 5 mM sodium citrate. Cells were again centrifuged, resuspended in MM1 with no carbon source, and plated directly onto freshly prepared nutrient agar plates containing 1 mM bromoethanol. Survivors were retained for liquid culture screening.

Generation of halohydrin dehalogenase negative mutants was achieved by further mutation of an alcohol dehydrogenase negative mutant. Following mutation and quenching, cells were resuspended in nutrient media for a 4 hours outgrowth at 30° C. Following two washes in MM1, cells were resuspended in the same containing 0.2 percent 2,3-dichloro-1-propanol and 50 units/mL of of penicillin G. Cells were incubated overnight with gentle agitation and survivors plated directly onto nutrient agar plates. Single colonies were transferred to nutrient media master plates and then replica plated onto minimal plates containing 0.2 percent 2,3-dichloro-1-propanol. Non-growers were retained for additional screening.

Enzyme Purification

One to two liter batches of wild type *Rhodococcus rhodochrous* was grown on a enriched media containing 1-chlorobutane to induce the dehalogenase. Five mLs of overnight grown inoculum prepared in nutrient media were inoculated into 250 mL of enriched media in a 1L flask, described earlier in "Culturing and Screening Methods" for the evaluation of cell free dehalogenase activities. Cultures were grown first for 24 hours followed by the addition of 50 μL of 1-chlorobutane. A second 50 μL of 1-chlorobutane was added at 48 hours, and cells were harvested by centrifugation at 72 hours. Cell pellets were stored frozen at −20° C. until use.

All purification steps were performed on ice or at 4° C. in a cold room. Enzyme activity was evaluated throughout using the procedure described in "Analytical Methods", except that 1,4-dichlorobutane was used as the substrate.

Frozen pellets from 2 liters of culture were thawed into 150 mL of 10 mM Tris sulfate buffer, pH=7.5 containing 1 mM disodium EDTA. This buffer was used throughout the entire purification. The suspension was sonicated for approximately 1 hour with ice cooling using a Microson Ultrasonic Cell Disrupter and centrifuged at 10,000 rpm for 15 minutes to remove cell debris. Supernatant was removed and the sonication/centrifugation repeated with fresh buffer to increase enzyme yield. Overall sonication efficiency was monitored by absorbence at 280 nm. Cell free extracts were combined and brought slowly to 30 percent saturation with solid ammonium sulfate. The suspension was centrifuged at 10,000 rpm for 30 minutes and the pellet discarded. The supernatant was brought to 70 percent saturation with solid ammonium sulfate and centrifugation repeated. Supernatant was discarded and the pellet taken up in a small volume of buffer and dialyzed overnight against 1 liter of the same. The preparation was applied to a 1.5×15 cm column of DEAE-Sephadex equilibrated with the same buffer elution carried out with a 1 liter gradient from 0 to 400 mM ammonium sulfate. Fractions of about 7-8 mLs were collected. The active fractions were pooled and brought to 90 percent saturation with ammonium sulfate. The pellet was taken up in a minimal amount of buffer, ultrafiltered to 2.5 mL using 10,000 MWCO Novacell Ultrafiltration cell, and applied to a 1.5×90 cm Sephadex G-100 column. Elution was by gravity at 90 cm and fractions of 7-8 mLs were collected. Active fractions were poled, brought to 30 percent saturation with ammonium sulfate, and applied to a 10 ml column of Butyl-agarose equilibrated in the same. Elution was performed with a 500 mL gradient from 30 percent-0 percent ammonium sulfate. Active fractions were pooled, dialyzed and used for substrate selectivity studies.

*Corynebacterium sp.* Strain m15-3, ATCC #43752 and *Xanthobacter autotrophicus* GJ10, ATCC #43050 were obtained from the American Type Culture Collection. Strain GJ70 was obtained from Dr. Dick B. Janssen, Department of Biochemistry, Groningen Biotechnology Center, University of Groningen, the Netherlands.

EXAMPLE 1

Biocatalyst Isolation and Selection

Enrichment studies were done utilizing 1-chlorobutane, 2-chlorobutane, and 1-chloro-2-methylpropane as a mixture for the sole sources of carbon. These substrates were chosen because (a) of their similar size to the preferred target compound (1,2-dichloropropane); (b) reactively non-toxic to microorganisms and; (c) the monohalogen compounds can be dehalogenated and assimilated by microorganisms. Utilizing the above enrichment techniques, 60 pure cultures were isolated from the various soil and water samples. The isolates utilized 1-chlorobutane as a sole source of carbon when grown in liquid culture with several cultures having growth rates from between about 0.14 to about 0.15 hour$^{-1}$. These growth rates indicate a high level of expression of a dehalogenating enzyme system.

The dehalogenation of haloalkanes by microorganisms can occur either by hydrolytic dehalogenation to give alcohols or oxygenolytic dehalogenation to give either aldehydes or methyl ketones after elimination of hydrochloric acid indicated as follows:

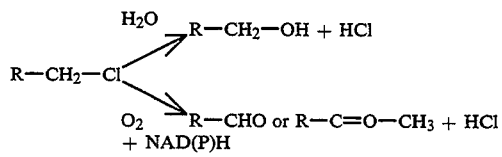

For biocatalyst development, it is desired to obtain the halohydrin and, thus preferably, for only hydrolytic dehalogenation to occur. To determine if dehalogenation was occurring by the hydrolytic route, cell free extracts from the 60 isolated strains grown on 1-chlorobutane were prepared and assayed for haloalkane dehalogenase activity by monitoring the release of free chloride from 1-chlorobutane. Only hydrolyric enzymes release chloride under these conditions since the oxidative system requires a reduced nicotinamide cofactors for catalysis.

Table I lists the results of cell free dehalogenase assays for seven of the organisms following growth and induction on 1-chlorobutane. Two controls, Corynebacterium species, ATCC 43752, and Acinetobacter species GJ-70, which are reported in the literature to contain a haloalkane dehalogenases, were included in the screen for comparative purpose.

TABLE I

SCREENING OF HALOALKANE DEHALOGENASE CANDIDATE ORGANISMS

| Organism | Chloride Release* (Ratio of 1,2-DCP to 1-Cl-Bu) (Percent) |
|---|---|
| PP-SF-002 | <0.5 |
| CF-P-001A | 1.3 |
| CFC-001B | 0.8 |
| SF-GP-001 | 2.6 |
| TDTM-002 | <0.5 |
| TDTM-003 | 5.8 |
| CFC-002 | <0.5 |
| ATCC 43752 | 1.6 |
| GJ-70 | 3.1 |

*Ratio of 1,2-dichloropropane to 1-Chlorobutane Hydrolysis in Cell Free Extracts Based on this data, strain designated TDTM-003, identified as a species of Rhodococcus by fatty acid analysis, was chosen for catalyst development.

Preliminary studies were performed on cell free extracts of TDTM-003 to evaluate the enzyme substrate selectivity, and the results of this study are shown in Table 2.

TABLE 2

Primary Screen of Dehalogenase Activity in Cell Free Extracts of *Rhodococcus Rhodochrous*, TDTM-003

| Substrate | Relative Rate of Chloride Release. 1-chlorobutane = 100 |
|---|---|
| 1-chloropropane | 57 |
| 1-chlorobutane | 100 |
| 1-chloro-2-methylpropane | 117 |
| 2-chloro-2-methylpropane | 2917 |
| 1-chloropentane | 109 |
| 1-chlorohexane | 136 |
| 1-chlorooctane | 159 |
| 1,3-dichloropropane | 203 |
| 1,4-dichlorobutane | 178 |
| 1,5-dichloropentane | 112 |
| 1,6-dichlorohexane | 169 |
| 1,10-dichlorodecane | 124 |
| 1-bromobutane | 362 |
| 1,2-dichloroethane | 2.8 |
| 1,2-dichloropropane | 4.2 |
| 1,3-dichlorobutane | 63 |
| 2,3-dichlorobutane | 73 |
| 1,2-dichlorobutane | 108 |
| 1,2-dichloro-2-methylpropane | 300 |
| 2-chlorobutane | 65 |
| 1,2,3-trichloropropane | 23 |

The results show that both 1,2-dichlorobutane (DCB) and 1,2,3-trichloropropane (TCP) have a higher relative chloride release rate than that of 1,2-DCP. Chloride was also released from several halohydrins in the presence of cell free extract.

EXAMPLE 2

Biocatalyst Development

Strain TDTM-003, as other cultures isolated in the enrichment program, does not utilize DCP as a sole source of carbon in liquid culture. When a 1-chlorobutane grown culture is presented with DCP, propylene halohydrins are detected in the broth by gas chromatography, at ppm levels.

Based on the known metabolism of DCP and 1,2-dichloroethane, one proposed route for halohydrin metabolism is through dehydrogenation by an alcohol dehydrogenase (ADH). ADH negative mutants were thus generated from TDTM-003 using nitrous acid as a mutagen.

Following mutation of TDTM-003 with nitrous acid, survivors were subjected to counter-selection using bromoethanol in either liquid or solid media as described by Janssen et al., *J. Bacteriol.*, 171:6791–6799 (1989). Four of eight mutants recovered from the protocol did not revert to growth on primary alcohols, such as ethanol, propanol or butanol, after 1–2 weeks exposure. These mutants had also lost the ability to grow on 1-chlorobutane. Furthermore, when these mutants were grown on succinate in the presence of 1-chlorobutane to induce the dehalogenase, 1-butanol accumulates in the broth. However, when the ADH negative mutants were grown and induced on succinate plus 1-chlorobutane and then challenged with either DCP, DCB or TCP, halohydrin products accumulated transiently but then disappeared.

The results indicated that a second pathway was involved in the degradation of the halohydrins. Glycidol was detected in the broth during the metabolism of TCP by these mutants. This provided evidence for a metabolic sequence as described by Wijngaard, et al., *J. Bacteriol*, 173:124–29 (1991), and represented by the following:

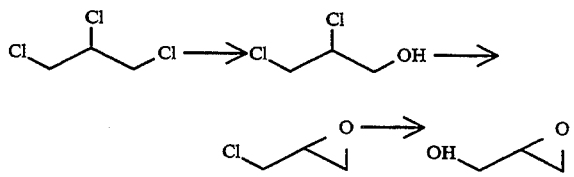

A second mutagenesis series was initiated utilizing an ADH negative mutant, designated TDTM-003-60, to select for halohydrin dehalogenase negative mutants. Following mutagenesis with nitrous acid and outgrowth on nutrient media, survivors were resuspended in minimal media containing 2,3-dichloro-1-propanol as a sole source of carbon in the presence of penicillin G. Counter-selection occurs as undesirable halohydrin dehalogenase capable mutants utilize the halohydrin for growth and are killed by the antibiotic. Survivors were rescued on enriched media followed by master plating onto the same. These were replica plated onto minimal media plates containing 2,3-dichloro-1-propanol as the sole source of carbon. Ten mutants were retained and their phenotypic inability to grow on 2,3-dichloro-1-propanol was confirmed in liquid culture. These putative "double" mutants were screened further on primary alcohols to confirm that the original ADH negative mutation had been retained. In contrast to the ADH negative mutants, these double mutants quantitatively accumulated halohydrins from the target substrates, DCP, DCB, and TCP.

A representative double mutant designated TDTM-003-60-2-11, made by the above example was deposited at the American Type Culture Collection on Jan. 28, 1993 and given the ATCC designation 55388. The biologically pure strain of TDTM-003-60-2-11 has a carbon utilization profile in liquid culture as shown in Table 3.

TABLE III

Utilization of Carbon Containing Compounds for Growth

| Carbon Source | TDTM-003 | TDTM-003-60-2-11 |
|---|---|---|
| Inositol | ++ | ++ |
| Maltose | ++ | ++ |
| Mannitol | ++ | ++ |
| Rhamnose | − | − |
| Sorbitol | ++ | ++ |
| p-Cresol | − | − |
| m-OH Benz | − | − |
| Pimelic Acid | ++ | ++ |
| Adipate | ++ | ++ |
| Benzoate | ++ | ++ |
| Citrate | ++ | ++ |
| Lactate | ++ | ++ |
| L-Tyrosine | − | − |
| Ethanol | ++ | − |
| Glycerol | ++ | ++ |
| Sucrose | + | + |
| Trehalose | ++ | ++ |
| Acetamide | + | + |
| p-OH-Benz | − | − |
| Sebacate | +/− | +/− |
| Fumarate | ++ | ++ |
| Gluconate | ++ | ++ |
| Malate | + | + |
| Pyruvate | ++ | ++ |
| Succinate | ++ | ++ |
| Dextrin | − | − |

TABLE III-continued

Utilization of Carbon Containing Compounds for Growth

| Carbon Source | TDTM-003 | TDTM-003-60-2-11 |
|---|---|---|
| Fructose | ++ | ++ |
| Glucose | ++ | ++ |
| Mannose | − | − |
| Adonitol | − | − |
| D-Arabinose | − | − |
| Cellobiose | − | − |
| Dulcitol | − | − |
| Galactose | − | − |
| Glycogen | + | + |
| Inulin | − | − |
| Lactose | − | − |
| Melezitose | − | − |
| Raffinose | − | − |
| Rhamnose | − | − |
| Xylose | − | − |
| DL-Norleucine | ++ | ++ |
| Octanoate | + | + |
| D-Mandelate | − | − |
| L-Serine | − | − |
| Hippurate | ++ | ++ |
| Malonate | − | − |
| L-Tryptophan | − | − |
| D-Glucosamine | − | − |
| Glycine | + | + |
| Benzamide | +/− | +/− |
| Cetyl alcohol | − | − |
| Stearate | + | + |
| Phenylacetate | + | − |
| Aminobutyrate | + | + |
| 1-Propanol | − | − |
| 1-Butanol | ++ | − |
| 2-methyl-1-propanol | ++ | − |
| 1,2-propanediol | ++ | ++ |
| 1,3-propanediol | ++ | − |
| 1,4-butanediol | + | − |
| 2,3-butanediol | ++ | ++ |
| 1,3-butanediol | + | − |
| 1,3-dichloro-2-propane | +/− | − |
| 2,3-dichloro-1-propane | +/− | − |
| 1-chloro-2-propanol | +/− | − |
| Arbutin | − | − |

++ indicates very good growth
+ indicates good growth
+/− indicates marginal growth
− indicates no visual growth A comparison with observations given in Bergey's Manual of Determinative Microbiolog, for Rhodococcus species *rhodochrous, erythropolis* and *fasicens* indicates similarity with TDTM-003-60-2-11, but does not fit the metabolic profile of these strains exactly. Fatty acid analysis indicated the closest similarity of the TDTM-003-60-2-11 to *Rhodococcus rhodochrous*.

EXAMPLE 3

Evaluation of Biocatalyst Kinetics and Selectivity

The double mutants were evaluated for conversion of DCP, DCB, and TCP following growth on succinate in the presence of 1-chlorobutane as an inducer of the dehalogenase. There was no substantial difference with respect to overall rate or product selectivity by the double mutants. For 80 to 100 hours, accumulation of halohydrins is linear, with no suggestion of product inhibition of the biocatalyst, within the concentration ranges of 5 to 100 ppm propylene halohydrins, 10–500 ppm butylene halohydrins and 10–300 ppm 2,3-dichloro-1-propanol. The in vivo rates of conversion for DCP vs. DCB vs. TCP were 0.30, 1.29, and 1.06 mg product/g dry cells/hr, respectively. The data indicated that TCP is exclusively dehalogenated at the primary carbon and only 3 percent of the DCB is dehalogenated at the secondary carbon. In contrast, DCP is preferentially dehalogenated at the secondary carbon with approximately a 3 to 1 selectivity.

Example 4

Biocatalyst Enantioselectivity

DCP and DCB are racemic mixtures, whereas TCP is an achiral meso compound. During transformation DCP or DCB by either the ADH negative mutants of TDTM-003 or the double mutants lacking both ADH and halohydrin dehalogenase activity, there is no indication of preferential conversion of one enantiomer over the other. Optical activity was not expected nor observed in the halohydrin products from 1,2-DCP and 1,2-DCB. However, when the conversion of racemic 2,3-dichloro-1-propanol was examined with the ADH negative mutants, uptake was found to be incomplete. This suggested that the halohydrin dehalogenase preferably accepts only one enantiomer of the racemic halohydrin. Furthermore, when ADH negative mutants were induced with 1-chlorobutane and then presented with TCP, 2,3-dichloro-1-propanol accumulates transiently but then completely disappears as glycidol begins to accumulate. This suggested that chirality is generated from TCP at the initial dehalogenating step. The observation was confirmed by isolating the 2,3-dichloro-1-propanol generated from TCP by a double mutant and examining optical activity by polarimetry and GC. Enantimeric excess was found to be 31 percent by polarimetry and 41 percent by GC analysis of diasteseomers.

EXAMPLE 5

Enzyme Purification and Substrate Selectivity

To evaluate the substrate selectivity of haloalkane dehalogenase from isolated Rhodococcus species, an enzyme preparation from the strain designated TDTM-003 was purified by the procedure described under General Experimental. This preparation provided a dehalogenase which was approximately 50 percent pure as estimated by SDS-PAGE and was free of interfering halohydrin dehalogenase activity. The amount of purification at each step of the purification is given in Table 4.

TABLE 4

| Fraction | Volume (ml) | Protein (mg/ml) | Protein (mg) | Activity Total* | Activity Specific** | Purification (fold) | Recovery (%) |
|---|---|---|---|---|---|---|---|
| Sonicate | 378 | 2.14 | 808 | 15.19 | 18.5 | 1 | 100 |
| 30–70% AS*** | 31.2 | 2.38 | 74.3 | 4.61 | 62 | 3.35 | 30.3 |
| DEAE-Sephadex | 167 | 0.10 | 16.7 | 4.41 | 264 | 14.3 | 29.0 |
| Sephadex G-100 | 13.1 | 0.46 | 6.0 | 2.99 | 496 | 26.8 | 19.7 |

TABLE 4-continued

| Fraction | Volume (ml) | Protein (mg/ml) | Protein (mg) | Activity Total* | Activity Specific** | Purification (fold) | Recovery (%) |
|---|---|---|---|---|---|---|---|
| Butyl-Agarose | 10 | 0.18 | 1.8 | 1.97 | 1094 | 59.0 | 13.0 |

*nmol Cl-/min
**nmol Cl-/min/mg protein
***AS = ammonium sulfate

The activity of this partially purified TDTM-003 dehalogenase preparation was evaluated against various chlorinated and brominated substrates. Each enzymatic rate was corrected for non-enzymatic hydroloysis. Results of this substrate profile are given in Table V.

TABLE V

Relative Rate of Halogen Release.
1-Chlorobutane = 100

| Compound | |
|---|---|
| 1-chloropropane | 33.000 |
| 1-chlorobutane | 100.000 |
| 1-chloropentane | 81.000 |
| 1-chlorohexane | 119.000 |
| 1-chloroheptane | 130.000 |
| 1-chlorooctane | 58.000 |
| 1-chlorodecane | 28.000 |
| 1,2-dichloroethane | 4.400 |
| 1,2-dichloropropane | 5.800 |
| 2-chlorobutane | 20.000 |
| chlorocyclohexane | 7.500 |
| 1,3-dichloropropane | 253.000 |
| 1,4-dichlorobutane | 261.000 |
| 1,5-dichloropentane | 173.000 |
| 1,6-dichlorohexane | 252.000 |
| 1,10-dichlorodecane | 52.000 |
| 1,2-dichloro-2-methylpropane | 0.000 |
| 1,2-dichlorobutane | 33.000 |
| 1,3-dichlorobutane | 81.000 |
| 2,3-dichlorobutane | 19.000 |
| 1,2,3-trichloropropane | 18.000 |
| 2,2-dichloropropane | 23.000 |
| 2-bromobutane | 123.000 |
| 1,2-dibromopropane | 900.000 |
| 1,2-dibromobutane | 756.000 |
| 1-bromo-2-chloroethane | 751.000 |
| 1-bromobutane | 265.000 |
| 1-bromopentane | 203.000 |
| 1-bromooctane | 414.000 |
| 1-bromodecane | 98.000 |
| 2-Bromopropane | 55.000 |
| 1,2-dibromoethane | 1318.000 |
| 1,3-dibromopropane | 771.000 |
| 1,4-dibromobutane | 294.000 |
| 1,6-dibromohexane | 244.000 |
| 1,8-dibromooctane | 173.000 |
| 1,3-dibromobutane | 155.000 |
| 2,3-dibromobutane | 846.000 |
| 1-bromopropane | 459.000 |
| 1-bromohexane | 162.000 |

A profile of substrate selectivities comparing the dehalogenase from TDTM-003 and the dehalogenase from *Rhodococcus erythropolis* as described in P. J. Sallis et al., *J. Gen. Mircobiol.*, 136:115–120 (1990), using 1-chlorobutane equal to 100, demonstrates the two enzymes as distinct, having a correlation coefficient of 0.731.

EXAMPLE 6

Dehalogenation of 1,2-dichloropropane by the double mutant strain of Rhodococcus sp., designated TDTM-003-60-2-11 was assayed in the following manner: 5 mL of an overnight culture (16 hours) were used as inoculum for 50 mL MM1X4P containing 5 g/L disodium succinate in a 250 mL flask. At 4 and 8 hours growth, 10 μL of 1-chlorobutane was added to induce the dehalogenase enzyme. Following 24 hours of growth, cells were harvested by centrifugation, resuspended into 50 mL of fresh MM1X4P, and transferred to a sterile 250 mL shake flask equipped with a bulb feeder. To the bulb feeder was added 1,2-dichloropropane and incubation continued at 28° C. and 150 rpm. The concentration of the substrate was usually in the 50–100 ppm range and did not exceed 200 ppm after 120 hours. The production of halohydrin products was monitored by gas chromatography. 1-Chloro-2-propanol and 2-chloro-1-propanol accumulate linearly in the culture broth to 74 parts-per-million (ppm) (w/v) and 20 ppm (w/v) respectively after 120 hours. The overall rate of halohydrin production is 0.60 mg/g dry cells/hr.

EXAMPLE 7

The procedure described in Example 6 was followed except 1,2-dichlorobutane replaced 1-chlorobutane in the bulb feeder. GC analysis showed 2-chloro-1-butanol accumulated linearly to 265 ppm (w/v) after 120 hours and 1-Chloro-2-butanol was found at a level of 6.5 ppm (w/v). The total halohydrin production rate was 2.47 mg/g dry cells/hr.

EXAMPLE 8

The procedure described in Example 6 was followed except 1,2,3-trichloropropane replaced 1-chlorobutane in the bulb feeder. 2,3-Dichloro-1-propanol was found to accumulate as the sole product to a level of 211 ppm (w/v) after 120 hours. The halohydrin production rate was 2.39 mg/g dry cells/hr.

The foregoing description of the preferred embodiment of the invention has been presented for purposes of illustration and description. It is not intended to be exhaustive or to limit the invention to the precise form disclosed. The embodiment was chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. A biologically pure culture of Rhodococcus species ATCC 55388 and mutants thereof capable of converting halogenated aliphatic hydrocarbons to primary halohydrins.

2. The biologically pure culture of claim 1, wherein the conversion is performed under mesophilic, aerobic conditions.

3. The biologically pure culture of claim 1, wherein the halogenated aliphatic hydrocarbons are selected from the group consisting of 1,2-dichloropropane, 1,2-dichlorobutane and 1,2,3-trichloropropane.

4. The biologically pure culture of claim 1, the culture being capable of converting a halogenated aliphatic hydrocarbon to a primary halohydrin in the presence of a liquid medium.

* * * * *